United States Patent [19]

Nakajima et al.

[11] Patent Number: 5,098,842
[45] Date of Patent: * Mar. 24, 1992

[54] MEDIUM, APPARATUS AND METHOD FOR CELL SEPARATION

[75] Inventors: Toru Nakajima; Masahiro Sato; Katsuhiko Nishimura; Sumiaki Tsuru, all of Tokyo, Japan

[73] Assignee: Asahi Kogaku Kogyo K.K., Tokyo, Japan

[*] Notice: The portion of the term of this patent subsequent to Aug. 2, 2005 has been disclaimed.

[21] Appl. No.: 145,667

[22] Filed: Jan. 14, 1988

Related U.S. Application Data

[63] Continuation of Ser. No. 850,186, Apr. 10, 1986, Pat. No. 4,761,366.

[30] Foreign Application Priority Data

Apr. 11, 1985 [JP] Japan .................... 60-77222

[51] Int. Cl.⁵ .................... C12Q 1/24; C12M 1/00
[52] U.S. Cl. .................... 435/287; 435/2; 435/30; 435/243
[58] Field of Search ............ 422/70; 423/307; 435/2, 435/30, 243, 287; 436/503, 161, 824; 501/1; 530/415; 210/656, 660, 667, 198.2

[56] References Cited

U.S. PATENT DOCUMENTS

| | | | |
|---|---|---|---|
| 3,737,516 | 6/1973 | Jenner | 530/415 |
| 4,097,935 | 7/1978 | Jarcho | 423/307 |
| 4,113,500 | 9/1978 | Ebihara et al. | 501/1 |
| 4,222,128 | 9/1980 | Tomonaga et al. | 501/1 |
| 4,330,514 | 5/1982 | Nagai et al. | 501/1 |
| 4,503,157 | 3/1985 | Hatahira | 401/95 |
| 4,629,464 | 12/1986 | Takata et al. | 501/1 |
| 4,654,314 | 3/1987 | Takagi et al. | 501/1 |
| 4,693,986 | 9/1987 | Vit et al. | 501/1 |
| 4,708,652 | 11/1987 | Fujiu et al. | 501/10 |
| 4,794,171 | 12/1988 | Tagaya et al. | 501/1 |
| 4,861,733 | 8/1989 | White | 501/1 |

OTHER PUBLICATIONS

Perry et al., *Perry's Chemical Engineer's Handbook*, Rev. 5th Ed., McGraw-Hill, Inc., 1984, pp. 20-78.

Chromatography, Electrophoresis, Immunochemistry, HPLC, Bio-Rad Laboratories (Richmond, CA), Price List J, Jan. 1984, pp. 39-44.

S. V. Hunt, in D. M. Weir (Ed.), Handbook or Experimental Immunology, 3rd Ed., Blackwell Scientific Publ., Oxford, 1978, pp. 24.10 and 24.11.

M. Spencer et al., Journ. Chromatog. 166, 425-434, 1978.

P. D. Wilkes et al., Journ. Dent. Res. 58, 1249, 1979.

*Primary Examiner*—David Saunders
*Attorney, Agent, or Firm*—Sughrue, Mion, Zinn Macpeak & Seas

[57] ABSTRACT

A sintered hydroxycalcium apatite body having an average particle size of 50-2,000 μm is used to form a packing in a cell separating column for use in separating groups or populations of cells from a suspension of animal cells.

2 Claims, 1 Drawing Sheet

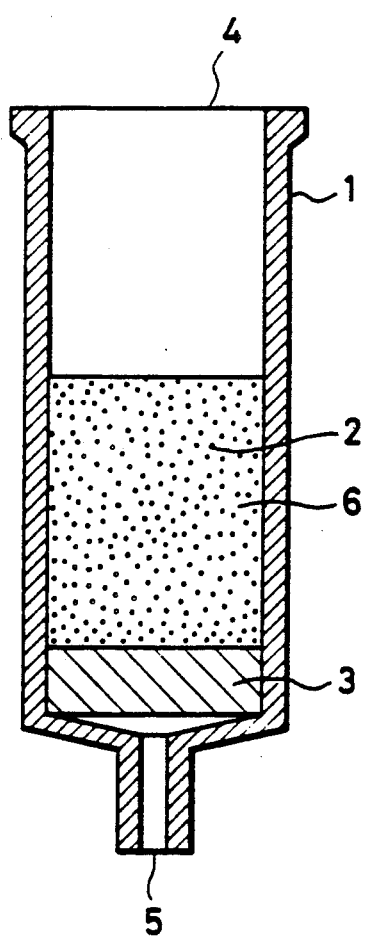

MEDIUM, APPARATUS AND METHOD FOR CELL SEPARATION

This is a continuation of application Ser. No. 850,186 filed Apr. 10, 1986, now U.S. Pat. No. 4,761,366.

BACKGROUND OF THE INVENTION

(1) Technical Field

The present invention relates to a medium, apparatus and method for separating a cell group, or a cell population or subpopulation of interest from a suspension of animal cells, in particular adhesive animal cells.

(2) Prior Art and Its Problems:

Separating a cell group of interest, i.e. a desired cell group type, or cell population or subpopulation, from a cell suspension is a routine practice conducted in the medical field, not only for the purpose of clinical testing but also with a view of performing immunodiagnosis or immunotherapy, including basic evaluation of a series of biophylactic potentiators. However, if one wants to separate T cells, B cells, K cells or NK cells from a suspension of lymphocytes, there is no reliable method available for doing so. Reliable, reproducible methods are unavailable for isolating a certain cell population while retaining the isolated cells in their original, that is, unchanged state. A strong need, therefor, exists for providing a technique which is capable of separating a cell population of interest in its unchanged state from a cell suspension.

Japanese Patent Application (OPI) Nos. 204454/82 and 140886/81 (the term "OPI" as used herein means an "unexamined published Japanese patent application") proposed techniques which are useful for obtaining T cells by a single stage of separation procedure using particulate materials having acidic functional groups or hydrophobic and water-insoluble particulate materials having micropores, more particularly, homo- and co-polymers of ethylene, propylene, vinyl chloride, vinyl acetate, styrene, divinylbenzene, acrylonitrils and methyl methacrylate, or nylon, polycarbonate, polyethylene terephthalate or polyester copolymers, or derivatives thereof, incorporating a sulfonic acid group, a carboxyl group, a phosphonic acid group or a phenol group. Problems experienced with these prior art cell separation techniques are that the column of particulate materials is easily plugged because of a small average particle size and that the chemical polymers per se or their residual low-molecular weight substances are toxic to the activity of the cells to be recovered.

While several materials and methods are authorized by international academic societies for use in separation of cells, all of them require considerable time and careful treatment in making preparation for separation procedures, involve complicated, time-consuming and laborious separating operations, and fail to provide a high degree of reproducibility because the resolution and its pattern (the spectrum of a cell population of interest) provided by the separating medium differs considerably from one production lot to another.

The Sephadex G10 process using a crosslinked dextran separation medium is one of the internationally approved methods for cell separation. Although the operating theory of this typical cell separating technique has not been completely unravelled, the principal role is believed to be played by the difference in adhesion to the dextran material between two cells such that macrophages or larger adhesive accessary cells are retarded by their relative adhesion whereas T cells or B cells do not adhere well to the dextran medium. However, in this method, non-adherent small accessary cells also do not adhere to the dextran medium. In addition, a recent study has revealed that some of the subpopulations of T cells are adherent on the dextran so that the T cell population cannot be obtained in its complete and integral form. This is a substantial drawback in attempt to use the Sephadex G10 process as an immunodiagnostic technique.

Another internationally approved cell separating device is a column packed with nylon wool. This column may be used as a means for obtaining a separated cell group abundant with T cells, but the substantial yield of the target cell that can be obtained by this column is generally low (12-25%). Although the purity of the T cell population obtained from this column is fairly high, the recovered T cell population differs from that in the original cell suspension. The column is used after being packed with a predetermined amount of nylon wool, but the resolution and its pattern will not only vary from one production lot to another but will also depend upon the manner in which the wool fibers are disintegrated, packed in the column or washed. It is to be noted that this problem of variations in characteristics is common to the organic separating mediums.

As will be understood from the foregoing brief explanation, commercial application of methods involving the separation of cells by making use of their adhesive nature has just begun. Higher process efficiency, speed and precision are expected to result from improving the separating method per se or the separating medium used, or from developing new materials suitable for use as separating mediums. Concerted efforts toward this goal are desired not only in the general field of biotechnology but also in important medical fields such as immunodiagnosis and immunotherapy.

SUMMARY OF THE INVENTION

One object, therefore, of the present invention is to provide a cell separation technique which is characterized by simplicity in preliminary treatment and procedures and in subsequent separation procedures.

Another object of the present invention is to provide an improved cell separation efficiency and a controlled separation pattern.

Still another object of the present invention is to provide a cell separation method having a higher degree of reproducibility and a material which is suitable for use in that method.

Other objects of this invention will be apparent from the detailed description of the invention hereinbelow.

As a result of concerted efforts made to attain the aforementioned objects, the present inventors have found that a sintered hydroxycalcium apatite body having a specified range of particle size exhibits a superior, varying adsorption activity for differing groups of immunological cells. The present invention has been accomplished on the basis of this finding.

In accordance with one aspect of the present invention, a cell separation medium is provided which is made of a plurality of discrete sintered hydroxycalcium apatite bodies having an average particle size of 50-2,000 $\mu$m.

In accordance with another aspect of the present invention, a cell separating apparatus is provided which is composed of a column that is packed with a cell separating medium made of a plurality of discrete sintered hydroxycalcium apatite bodies having an average particle size of 50–2,000 μm, said column having an inlet and an outlet for a cell suspension and being provided with a filter for preventing dispersion of said cell separating medium.

In accordance with a further aspect of the present invention, a cell separating method is provided which comprises bringing a cell suspension into contact with a cell separating medium of a packing of a plurality of discrete sintered hydroxycalcium apatits bodies having an average particle size of 50–2,000 μm, thereby permitting a cell population of interest to be adsorbed on said cell separating medium.

DESCRIPTION OF THE DRAWING

The FIGURE of the Drawing represents a cross-sectional view of a cell separator in accordance with one embodiment of the present invention, wherein column 1 is packed with a separating medium 6 made of sintered hydroxycalcium apatite bodies 2, the separator being equipped with a filter 3 and having both an inlet 4 and an outlet 5 for the cell suspension.

DETAILED DESCRIPTION OF THE INVENTION

The sintered hydroxycalcium apatite body used in the present invention should have an average particle size in the range of 50 to 2,000 μm. If the average particle size of the sintered body is less than 50 μm, insufficient flowability causes a high incidence of a clogging problem depending upon the size of the cells to be separated and the form of blast cells. If, on the other hand, the average particle size of the sintered hydroxycalcium apatite body exceeds 2,000 μm, the surface area available for adsorption is decreased to give a degraded resolution.

The sintered hydroxycalcium apatite body used in the present invention preferably has such a composition that the Ca to P ratio ranges from 1.4 to 1.8. If the Ca to P ratio is less than 1.4 or more than 1.8, the adsorption capacity of the apatite is decreased, causing a drop in the resolution to an undesirably low level.

The sintered hydroxycalcium apatite body used in the present invention is preferably prepared by firing hydroxycalcium apatite particles at a temperature within the range of 600° to 1,350° C. If the firing temperature is less than 600° C., the resulting apatite has a reduced adsorption for monocytes. If the firing temperature exceeds 1,350° C., the apatite is degraded and an integral ceramic body cannot be produced. After firing, granulation is carried out to the designated particle size range.

In accordance with the present invention, cells of interest can be separated without being stimulated immunologically, and the cell recovery and resolution that are attained are much higher than are possible with the prior art techniques. The separation procedures are substantially simplified, with the time required for complete separation being reduced to a fraction of the time required by the conventional techniques. Because of the very small water retention of the separating medium employed, the method of the present invention permits the use of a one-step recovery process. The cell suspension may be directly caused to flow into the separating medium, which even may remain unwashed if permitted by the separation object. The separating medium (which can be sterilized by heating at any temperature between 100° and 500° C.) may be assembled with a sterilized column (which may be a syringe if small-scale separation is performed) into a ready-to-use state in a very simple manner and within a short period of time. This feature affords a highly economic advantage in terms of preparatory operations. If desired, the separating medium and other necessary components are packed into a disposable column and the assembled kit may be placed on the market in a completely sterilized condition.

Although applicants do not wish to be bound by a theory explaining the operation of the invention, the ability of the sintered hydroxycalcium apatite to adsorb a group of immunological cells is believed to derive from the fact that this substance is the same as the principal component of bones in vertebrates. This substance is a bioactive material, believed optimal for use as a material for separating adhesive cells because, as far as is known, no other materials can compete with the hydroxycalcium apatite in terms of the specificity of adsorption of living cells thereto, degree of adhesion thereof and the controllability of such cell adsorption and adhesion.

In one embodiment of the present invention, polysaccharides and mucopolysaccharides derived from the living body such as hyaluronic acid, chondroitin sulfate, chitin derivatives, fibronectin and osteonectin, and derivatives thereof, may be partly adsorbed on the surfaces of the granules of the sintered hydroxycalcium apatite, to modulate the physicochemical or immunological properties of the substrate surface, such that it acquires subtly changed activities of adsorption for different cell groups of interest. This permits the resolution characteristics of the column to be effectively varied so as to provide sharp elution patterns or controlled resolution spectra. In addition, the adsorption properties of the hydroxycalcium apatite for the respective subpopulations of a cell group of interest are modulated or fine-tuned such that it becomes possible to selectively separate a specific cell subpopulation.

With a column intended for treating a large quantity of cells, the rate of passage of the cell suspension can be rendered freely adjustable by incorporating a multistage cascade configuration, or a structure affording uneven distribution in the adsorption characteristics, or a U-shaped tube system. In order to obtain a fine resolution pattern, the column may be placed in a state of weightlessness so as to permit the passage of the cell suspension solely by diffusion and without convection.

EXAMPLES OF THE INVENTION

The present invention is hereunder described in greater detail with reference to working examples where it is applied to the separation of lymphoid cells. It should be noted that the concept of the present invention is also applicable to the separation of other adhesive cells.

The following working examples were carried out using a cell separator having the configuration shown in the accompanying drawing. As shown, the cell separator consists of a column 1 that is packed with a separating medium 6 made of sintered hydroxycalcium apatite bodies 2, the separator being equipped with a filter 3 and having both an inlet 4 and and outlet 5 for the cell suspension. The filter 3 is typically made of a gas-permeable porous member or fibers selected from among plastics, glass, ceramics, etc.

EXAMPLE 1

A column having an internal capacity of 5 ml was packed with 0.02 gr. of glass wool which occupied 0.08 ml of the column capacity. As it was tapped, the column was subsequently filled with packing sintered (firing temperature: 700° C.) hydroxycalcium apatite bodies (Ca/P=1.67) having an average particle size of 400-500 μm, such that the apatite would occupy 5 ml of the column capacity.

The so-assembled cell separator was washed by successive passage of physiological saline solution, a culture medium (RPMI 1640) held at 37° C. and which contained 10% of fetal bovine serum.

Subsequently, monocytes separated from the normal human peripheral blood by specific gravity centrifugation were suspended in a culture medium (RPMI 1640) containing 10% of fetal bovine serum. A predetermined portion (0.4 ml) of the cell suspension was loaded onto the column, allowed to permeate through it, and incubated at 37° C. for 1 hour. The cells were subsequently eluted with a culture medium (RPMI 1640).

The resolution of the monocytes by the cell separator was evaluated by the following two methods. In one method, the number of cells was counted with a hemocytometer both before and after the passage of the cell suspension through the column. The cell recovery data obtained by this method are shown in Table 1. The other method consisted of examining the state of cell separation: the cells in the effluent from the column were labelled with fluorescein-tagged anti-bodies, Leu 1, Leu 12 and Leu, M3, and the positivity for T cells, B cells and monocytes was determined with FACS (fluorescence activated cell sorter). The results of estimation by this method are shown in Table 2.

EXAMPLE 2

A column having an internal capacity of 5 ml was packed with 0.02 gr. of glass wool which occupied approximately 0.8 ml of the column capacity. As it was tapped, the column was subsequently filled with a sintered (firing temperature: 1,200° C.) hydroxycalcium apatite body (Ca/P=1.67) having an average particle size of 400-500 μm such that the apatite would occupy 5 ml of the column capacity.

Using the so assembled cell separator, human monocytes were separated and their resolution evaluated as in Example 1. The results of evaluation of monocytic resolution are shown in Tables 1 and 2.

EXAMPLE 3

A column having an internal capacity of 5 ml was packed with 0.02 gr. of glass wool which occupied approximately 0.8 ml of the column capacity. As it was tapped, the column was subsequently filled with a sintered (firing temperature: 700° C.) hydroxycalcium apatite body (average Ca/P=1.67) having an average particle size of 800-1,000 μm such that the apatite would occupy 5 ml of the column capacity.

Using the so-assembled cell separator, human monocytes were separated and their resolution evaluated as in Example 1. The results of evaluation of monocytic resolution are shown in Tables 1 and 2.

EXAMPLE 4

A column having an internal capacity of 5 ml was packed with 0.02 gr. of glass wool which occupied approximately 0.8 ml of the column capacity. As it was tapped, the column was subsequently filled with a sintered (firing temperature: 700° C.) hydroxycalcium apatite body (average Ca/P=1.67) having an average particle size of 400-500 μm such that the apatite would occupy 5 ml of the column capacity.

Using the so-assembled cell separator, human monocytes were separated and their resolution evaluated as in Example 1. The results of evaluation of monocytic resolution are shown in Tables 1 and 2.

COMPARATIVE EXAMPLE 1

A column having an internal capacity of 5 ml was packed with 0.25 gr. of nylon wool which occupied approximately 3 ml of the column capacity. Using the so-assembled cell separator, human monocytes were separated and their resolution evaluated as in Example 1. The results of evaluation of monocytic resolution are shown in Tables 1 and 2.

EXAMPLE 5

A column having an internal capacity of 5 ml was packed with 0.02 gr. of glass wool which occupied approximately 0.8 ml of the column capacity. As it was tapped, the column was subsequently filled with a sintered (firing temperature: 700° C.) hydroxycalcium apatite body (Ca/P=1.67) having an average particle size of 400-500 μm such that the apatite would occupy 5 ml of the column capacity. After assembling the cell separator by these procedures, human monocytes that were collected as in Example 1 were passed through the separation column in an amount of 1 ml ($1.8 \times 10^7$ cells) and, after elution with a culture medium (RPMI 1640), the cells in the effluent were recovered.

The monocytic resolution of the column was evaluated as in Example 1, and the results are shown in Tables 1 and 2.

The results of Examples 1, 3, and 4 show that the use of the sintered hydroxycalcium apatite body as a separation medium contributed to the accomplishment of high recovery and resolution. The recovery data obtained in these examples were remarkable compared with Comparative Example 1 wherein nylon wool was used as a separating medium. The result of Example 2 shows that by employing a higher firing temperature in the making of the hydroxycalcium apatite, contamination of the column effluent by monocytes could be held to a minimum (0.8%). The result of Example 5 demonstrates that the cell separator of the present invention allows high recovery and resolution to be obtained even if it is not given such treatments as washing and incubation.

TABLE 1

| Cell Recovery | |
|---|---|
| Run No. | Recovery (%) |
| Example 1 | 95 |
| Example 2 | 50 |
| Example 3 | 90 |
| Example 4 | 85 |
| Comparative Example 1 | 30 |
| Example 5 | 90 |

TABLE 2

| | Positivity | | |
|---|---|---|---|
| Run No. | T cell (Leu 1) | B cell (Leu 12) | Monocyte (Leu M) |
| Example 1 | 94 | 3.5 | 2.3 |
| Example 2 | 95 | 3.5 | 0.8 |

TABLE 2-continued

| Run No. | Positivity | | |
|---|---|---|---|
| | T cell (Leu 1) | B cell (Leu 12) | Monocyte (Leu M) |
| Example 3 | 95 | 3.0 | 1.0 |
| Example 4 | 95 | 2.0 | 0.9 |
| Comparative Example 1 | 95 | 1.7 | 1.4 |
| Example 5 | 94 | 3.0 | 1.0 |

ADVANTAGES OF THE INVENTION

As will be apparent from the foregoing description, the sintered hydroxycalcium apatite body having the specified range of particle size which is used as a cell separating medium in the present invention allows a cell population of interest to be separated without being stimulated immunologically, and the cell recovery and resolution that are attained are much higher than are possible with the prior art techniques. In addition, this separating medium has a very small water retention and permits the use of the one-step recovery process wherein the cell suspension is directly caused to flow into the separating medium, which may even remain unwashed if the separation object so permits. Therefore, the method of the present invention can be practiced with substantially simplified separation procedures. If desired, a variety of substances may be partly adsorbed on the surfaces of granules of the sintered hydroxycalcium apatite and the physiochemical or immunological properties of the substrate surface are modulated such that it acquires subtly changed activities of adsorption for different cell groups of interest. This permits the cell separation efficiency to be further improved, or the production of controlled resolution patterns.

Variations of the invention will be apparent to the skilled artisan.

We claim:

1. A cell separating apparatus which comprises a column that is packed with a cell separating medium formed of discrete sintered hydroxycalcium apatite bodies having an average particle size of 400 to 2,000 $\mu$m, said column having an inlet and an outlet for a cell suspension and being provided with a filter for preventing dispersion of said cell separating medium wherein said sintered hydroxycalcium apatite body has a calcium to phosphorus (Ca/P) ratio within the range of 1.4 to 1.8.

2. A cell separating apparatus according to claim 1 wherein said sintered hydroxycalcium apatite bodies are prepared by firing hydroxycalcium apatite particles at a temperature between 600° and 1,350° C. and by subsequent granulation of the fired apatite.

* * * * *